United States Patent [19]

Sjogren

[11] Patent Number: 5,484,600
[45] Date of Patent: Jan. 16, 1996

[54] INSECTICIDAL COMPOSITE TIMED RELEASED PARTICLE

[75] Inventor: Robert D. Sjogren, St. Paul, Minn.

[73] Assignee: Merdian, L.L.C., Minneapolis, Minn.

[21] Appl. No.: 375,859

[22] Filed: Jan. 20, 1995

[51] Int. Cl.$^6$ ................................................. A01N 25/00
[52] U.S. Cl. .................. 424/405; 424/93.461; 424/93.1; 424/93.46; 424/409; 424/418; 424/468
[58] Field of Search ............................ 424/405, 93.461, 424/93.1, 93.46, 409, 405, 418, 468

[56] References Cited

U.S. PATENT DOCUMENTS

| | | | |
|---|---|---|---|
| 147,615 | 2/1874 | Dayton | 424/409 |
| 3,127,235 | 3/1964 | Benzel et al. | 422/28 |
| 3,420,933 | 1/1969 | Cords et al. | 424/84 |
| 4,631,857 | 12/1986 | Kase et al. | 43/132.1 |
| 4,650,792 | 3/1987 | Underwood | 514/89 |
| 4,732,762 | 3/1988 | Sjogren | 424/409 |
| 4,865,842 | 9/1989 | Bradbury et al. | 424/408 |
| 4,971,796 | 11/1990 | Sjogren | 424/417 |
| 5,283,060 | 2/1994 | Shieh | 424/418 |

OTHER PUBLICATIONS

*Mosquito News*, vol. 44, No. 1, Sustained Release Formulations of *Bacillus sphaericus* and *Bacillis thuringiensis* (H–14) For Control of Container–Breeding Culex Quinquefasciatus[1], Mar. 1984, pp. 26–32.
1983 Annual Report Mosquito Control Research, University of California Evaluations of BTI formulations for mosquito control, pp. 52–53.
Applied and Environmental Microbiology, Apr. 1987, vol. 53, No. 4, p. 828, Fate of Bacillus thuringiensis subsp. israelensis under Simulated Field Conditions.
*Vector Ecology Newsletter,* 1989, Enhancement of *Bacillus thuringiensis* and *Bacillus sphaericus* Persistence with Slow–Release Formulations.
*Operational and Scientific Notes,* reprinted from Mosquito News, vol. 44, No. 2, Jun. 1984, pp. 236–239.
Vectobac®–G, Biological Mosquito Larvicide, Granular Formations Feb. 1986.
*Journal of the American Mosquito Control Association,* Sep. 1986, vol. 2, No. 3, pp. 376–378.

*Primary Examiner*—Thurman K. Page
*Assistant Examiner*—Pamela S. Webber
*Attorney, Agent, or Firm*—Merchant, Gould, Smith, Edell Welter & Schmidt

[57] ABSTRACT

A composite particle timed release pest control agent comprising a dense core particle, a floatation particle, a pesticide, and a composite forming adhesive. The density of the core particle adapts the composite for broadcast application to aqueous and periodically flooded treatment locus and causes the composite to penetrate foliage to contact environmental water. After contact with water at a treatment locus, water causes the adhesive to soften disassembling the composite particle releasing the floatation particle and the pesticide to the surface of the environmental water. At the surface the dissolution rate of the adhesive causes a timed release of the pesticide for action. The composite particle of the invention can be formulated in a quick release formulation that releases the active pest control agent for control in a one to twelve day period or within 0.1 to 72 hours. A long lasting slow release composite can be manufactured that can be used to obtain effective pest control for 10 to 30 days. In a preferred mode, a bacterial pest control agent is used to control mosquito populations during prime mosquito hatching.

46 Claims, No Drawings

INSECTICIDAL COMPOSITE TIMED RELEASED PARTICLE

FIELD OF THE INVENTION

The invention relates to a timed release pest control composite and to methods of controlling pests with a particulate composite. The pest control composite is manufactured from materials that result in a composite that can be applied by broadcast techniques, for example, by hand and from aircraft into aqueous sites, wet-lands, or dry sites that have episodic rainfall. The particle in contact with water releases the pest control agent to the surface of the environmental water for effective pest control. The composite can be formulated to provide quick pest control activity (0.1–72 hours), intermediate effective lifetime (1–12 days) or long term pest control activity (10–30 days).

BACKGROUND OF THE INVENTION

During the temperate months of the year many pest populations in various areas of the United States reach levels causing severe problems. One pest, the mosquito, can be distracting, can cause bites which itch and in certain areas can be a vector for the spread of communicable diseases such as equine encephalitis, malaria, etc. Mosquito populations vary during temperate periods depending upon species, rainfall, temperature and other conditions. While the life span of an adult mosquito is not long, mosquito larva can continually mature throughout the year into the adult stage, resulting in the continuing resupply of the adult mosquito population. Further, due to the presence of a large variety of different mosquito species and differing maturation times and rates, mosquito pests can be present during much of the temperate season.

Many communities have combated mosquito populations and other pests by fogging or spraying the environment with an insecticide, adding insecticide to likely hatching sites, and by distributing a variety of immediate to slow release insecticide compositions into the environment. The treatment of large areas of the environment having significant numbers of trees, shrubs and other vegetation requires a particulate form of pest control agent to effectively control population. A pest control agent in the form of dense granules is preferred in aerial applications. Such dense granules permit accurate application of the pest control agent in winds up to 14 miles per hour. The dense granules permit penetration of dense vegetation canopies and reduce uneven application (drift) caused by variations in winds and turbulence. During the breeding season, dense granules can be used to regulate the rate of pesticide release in an environmental body of water over an extended period of time. In another environment, the pest control means can be applied to a dry site that experiences periodic flooding. The composite particle while wet can release significant proportions of pesticide.

Many other pests can cause severe problems during their growth or reproductive cycles. Such cycles generally correspond to the temperate seasons of the year and are often triggered by the presence of moisture. Mollusks in both the old and larva forms can infest fresh water damage flora and fauna, provide a diseased vector and impose cosmetic problems. Fungi and algae grow rapidly in fresh water and can make water unpleasant for recreational purpose, may produce toxins which poison farm animals and can make water unfit for human consumption. A variety of plants can grow in unwanted areas, reducing crop yields and presenting weed control problems in many residential and agricultural environments. Many attempts have been made to combat these pests with pest control devices using a variety of pesticides.

Pesticides have been encapsulated with both macro and microencapsulation processes, placed in ceramic materials, included in biodegradable polymers, mixed with porous mineral supports, coated with cellulosic derivatives, combined with polyuria compounds, and included with gypsum and other supports to protect the pesticide from the environment and to ensure a controlled release in an attempt to substantially control pest populations. Sjogren, U.S. Pat. No. 4,732,762, teaches a slow release pest control composition comprising an encapsulated pesticide, carbon and a plaster. The high compressive strength plaster causes a slow release of the materials into the environment. Sjogren, U.S. Pat. No. 4,971,796, teaches a layered pest control agent comprising a core particle and layered on the core particle, intermediate spacing layers of a proteinaceous layer and an intermediate spacing layer, the proteinaceous layer containing pesticide.

For the purpose of this invention, a pesticide is considered any material, compound, composition, bacteria, virus, or other chemical or bio-active material that can act to reduce populations of a pest in an infested locale. An effective pest control concentration is defined as a concentration effective to kill a substantial proportion of at least one stage or form of a pest during its life cycle, or a concentration effective to prevent the development or maturation of one or more stages of the pest during its life cycle. The pesticide should be released by the pest control means at a substantially even rate during a treatment, such that an effective concentration is released but the pesticide is not wasted. In areas of dense vegetation, the pest control means is preferably of small size, about 0.5 to 10 millimeters in diameter, to permit even distribution and penetration of dense vegetation in environmental areas where pest control applications are needed. The pest control means should have a density that permits easy penetration of dense vegetation and precise application even in high or variable wind conditions. The pesticide composition and means should comprise natural materials, be biodegradable and of low cost.

Accordingly, a substantial need exists for a controlled release pest control composition that can be made into a granular control means, can be supplied by aircraft or by hand or other machine broadcast techniques. A further need exists for a pest control agent that is of sufficient density to be easily applied to environmental locations, can be applied to either wet or dry locales but can release an effective pest control concentration of pesticide into environmental water. Still a further need exists for a pest control means that can provide substantial control of pest populations in a quick release mode, from 0.1 to 72 hours, an intermediate release, for 1- 12 days, or in a long lasting slow release mode, for 10–30 days. Finally, a need exists for a granular pest control composition where significantly less materials per acre applied still results in substantial control of pest populations. The granule should protect the pesticide from substantial degradation, provide for uniform distribution of the pest control means and sustain controlled release of the pesticide in any environment.

BRIEF DISCUSSION OF THE INVENTION

I have found a pest control means that comprises a composite particle, granule or pellet formed by bonding particles using a water soluble or water sensitive adhesive material. The composite particle comprises at least one heavy particle of density substantially greater than water, a floatation agent having a density less than water, and a pesticide. The particles are combined into a composite granule using a water soluble or water sensitive adhesive. The water soluble adhesive maintains the particles in a composite of high density, e.g. greater than 1.10 g/ml, that can be easily applied through dense vegetation to aqueous sites using a variety of airborne, ground vehicle, or hand broadcast techniques. The particle can easily be applied to bodies of environmental water or to areas that are periodically flooded. In contact with water, the adhesive is dissolved, softened or attenuated by water to the degree that the particles are released from the composite. Upon release, the floatation particle carries the pesticide to the surface of the body of water or distributes the pesticide via terrestrial soil and foliage and interstitial water where the pesticide acts to control pest populations. For reasons of ease of manufacture and controlled distribution of the pest control means, the pest control means takes the form of a regular, generally uniform particle composite. The composite can be manufactured with varying release rates depending on the nature of the adhesive used. The type of adhesive, adhesive molecular weight, crosslinking, and concentration of adhesive can be selected such that the adhesive has a desired quick or slow dissolution or release rate. The decomposition or dissolution of the water soluble or water sensitive adhesive is most effective and uniform when the pest control means is fully immersed in free standing environmental water. However, interstitial water present in soils can similarly cause the release of the pesticide. For the purposes of this invention, the term pest is intended to cover any living organism, plant, animal or microbe, whose presence causes human discomfort, harm to agriculture, a health hazard, or cosmetic harm.

The invention also includes a process for the manufacture of a pest control timed release composite particle by prilling the core particle in a mixing apparatus; spraying the prilled core particle with an aqueous solution of the water soluble adhesive. Spraying is carried out lightly with a fine spray using, for example, flat fan spray nozzles with pressure appropriate to deliver the entire liquid volume in a fine fan spray within a certain period of time, depending on the batch size. Concurrent with the spraying of the adhesive, a floatation agent admixed with the pesticide is added preferably as a mixed powder, with a vibratory unit at approximately the same rate of addition as the spray delivery rate of the adhesive solution. When the addition of the materials is complete, the resulting particles or prilled granules are rolled for at least a minute or longer. If desired, a drying agent may be added with the floatation agent and pesticide above or at this stage followed by additional rolling of the prilled composite particle or granules. The drying agent, when needed, is added in amounts required by the finished granule moisture level and ambient relative humidity conditions to maintain a free flowing granule after compacted in storage.

DETAILED DISCUSSION OF THE INVENTION

The timed or controlled release pesticide composite of the invention comprises a high density component or core, a floatation particulate, a pesticide particulate, and a water soluble or sensitive composite forming adhesive. The composite can further contain a surfactant, sunscreen, a drying agent, or other material that can aid in varying the release role, maintaining stability, stabilizing the particle during storage and use or providing other beneficial attributes.

Core

The controlled release composite contains a high density core particle. A core particle should be selected that provides sufficient density to the composite resulting in a composite that sinks when placed in standing water. The density of the core particle is thus greater than water and, preferably, greater than 1.10 g/ml. The core is preferably inactive, an inert or solid core which provides added weight not only to sink it to the bottom of bodies of water but also beneficial for application of the composite over an intended area from the air by helicopter or airplane.

Another consideration which affects the choice of materials used for the core is the available surface area required of the core particle. Specifically, the core must have adequate surface area to allow coating of the adhesive, pesticide and floatation agent as will be discussed below.

Generally, given the considerations of mass and surface area, the core may be anything that has a certain internal or surface particle size. The desirable particulate core has a diameter ranging from about 1 mm to 4 mm (20–40 to 8–16 mesh). Specific types of materials which may be used are sand, limestone granules, clay, gypsum, or fine sand pearl balls.

As an alternative embodiment of the present invention, the above defined particle may be the controlled release composite as a single particle and act as a core. Thus, for example, a high density fine powder, such as fine sand, may be coblended with a floatation agent and a pesticide, both in powdered form. A water soluble composite forming adhesive is sprayed onto the blend by a pan agglomeration method known in the art to form an agglomerate particle or the mixture may be compressed to a particle such as a pellet. The resulting particle being the controlled release composite may have the same particle size as described above or up to about 15 mm. and a density of greater than about 1.10 g/ml.

As an example, fresh made granules (particles) prepared by both embodiments of the invention have a density of about 1.7 to 1.8 g/ml. and dry granules about 1.4 to 1.5 g/ml.

Pesticide

The term pesticide as employed here is intended to include any active material used for control of unwanted plants, insects, animals, or microorganisms, such as mosquitoes, snails, weeds. Included among pesticides are in particular insecticides, herbicides, biocides, e.g. bacteria, viruses, fungi and nematodes, and other biological control agents or management materials utilizable in the environment.

A great variety of pesticides can be used in the present invention which are compatible with the water soluble adhesive and floatation agent of the invention. Representative of the pesticides which may be employed are those disclosed in U.S. Pat. No. 4,971,796 which is incorporated herein by reference.

A preferred embodiment of the present invention has been found to be a bacterial pesticide. Such a pesticide offers significant advantages for selective control of invertebrate pests of economic importance with low environmental impact. One such bacterial pesticide is a *Bacillus thuringiensis*. Of particular importance is *Bacillus thuringiensis israelensis*, (Bti) which has been commercially developed for control of mosquito and black fly larvae. An additional *Bacillus thuringiensis* also found of value is *Bacillus thuringiensis var kurstaki*. These bacteria kill target insects when ingested during feeding. The above bacteria are also especially compatible with the floatation agents and water soluble adhesives of the present invention and described below. As an example the Bti strain is available as a primary powder with varying toxic unit potencies. Preferably international toxic unit potency of 6,000 to 10,000 or higher is employed in the composite of the present invention.

Water Soluble Adhesive

The water soluble adhesives of the present invention are those tacking agents that are compatible with the pesticide and floatation agent and can adhere to the core particle. Examples of such are technical protein colloids, animal colloids/gelatins, polyvinyl alcohol, dextrin, and the like. Colloid proteins such as those described in U.S. Pat. No. 4,971,796 can be used in the present invention. This reference has been incorporated herein above. An advantage of using colloid proteins is that they provide a protein feeding stimulus to target organisms to increase pesticide ingestion.

The preferred adhesive is, for example, a technical protein colloid which will provide in the composite of the present invention sustain slow release of the pesticide over a period of time of approximately 10 to 30 days.

On the other hand, for quick release of pesticide, a preferred embodiment is, for example, a gelatin such as fish gelatin or colloid which in the present composite will provide release of the pesticide anywhere from 0.1 to 72 hours. Such a fish gelatin can, for example, be obtained from Norland Products, Inc. as HIPURE Liquid Gelatin. The fish gelatin product from Norland is a protein molecule containing a complex chain of 20 amino acids with an average molecular weight of 60,000. The gelatin is very water soluble and is available in both liquid and solid powder forms. The gelatin also has high initial tack properties. In the preparation of a composite of the present invention, the above adhesive is preformulated in an aqueous solution and may contain further ingredients which add to the benefit of the adhesive and the total composite. The solution is sprayed onto the core particle as is described in more detail below.

When the water soluble adhesive is a colloid, it optionally may be reacted with an aldehyde to increase apparent molecular weight and reduce water solubility, if desired, depending on the release rate desired. Thus the addition of aldehydes such as formaldehyde or glyoxal may be added to the collagen solutions which can significantly and proportionally reduce the water solubility of subsequently dry collagen and hence be used to regulate the dissolution of colloids containing pesticides in finished formulations. The use of such crosslinking agents is also described in U.S. Pat. No. 4,971,796 which reference has already been incorporated herein.

In addition, water, and/or wetting/dispersing agents may be used. Particularly, it has been found that anionic surfactants are important and useful wetting agents in the present composite when mixed in a solution containing a water adhesive. As a preferred anionic surfactant, an alkyl sulfate or alkyl aryl sulfonate or mixtures thereof may be used. The amount of anionic surfactant may vary but may be anywhere from 0.0 to 0.5 wt %. More preferably, the surfactant may vary from 0.005 to 0.4 wt % of the total composite.

Plasticizers may also be employed in the aqueous adhesive solution such being, for example, polyols such as propylene glycol or preferably glycerine. The polyol used in a composite may vary in amounts from 0.05 to 3.0 wt %. Preferably, a range of 0.05 to 2.0 wt % is employed based on the total composite.

Floatation Agent

A variety of floatation or buoyant agents of different types and sizes may be used to deliver the pesticide or microbial agents from the bottom of bodies of water or flooded sites to the water surface or free water on terrestrial soil surfaces where they are released for best target insect contact. These agents are uniform in size but may vary from about 1 to 500 microns, preferably 10 to 100 microns, and must have a specific gravity or density less than water, preferably less than 0.9 g/ml. Examples of such agents are perlite, polypropylene powder, and cork powder. A preferred agent is a perlite product obtained from Grefco, called Dicaperl HP 920.

If desired, the composite of the present invention may also contain a drying agent. A drying agent such as amorphous silica may be used in the composite. The drying agent is added as needed preferably in the last step of the formulation, described below, or coblended with pesticide and buoyant agent powders. Depending on the texture of the finished composite particle or granule moisture level and ambient relative humidity conditions, the drying agent maintains a free flowing granule after compacted in storage.

As stated above, the finished composite product is administered by broadcast means preferably by helicopter or airplane but can also be administered by ground vehicle, mechanical spreaders or by hand to bodies of water or known mosquito breeding sites which are likely to be flooded with water or terrestrial sites where pools of water may form from rainfall. After contact with water at the treatment locus, the particle sinks to the bottom and the water causes the adhesive to soften disassembling the composite particle and releasing the floatation agent in admixture with the pesticide to the surface of the body of water. At the surface, depending on the adhesive used, the dissolution rate of the adhesive causes a timed release of the pesticide for action.

An important advantage of the finished composite product is efficacy. Significantly less granules per acre of the present invention are required to provide greater than 90% pest control. Administration of pesticides to sites mentioned above for effective pest control often require about 10–20 lbs. per acre of material. Due to the multiple particulate release of the buoyant agent, it has been found that administration of about 3–6 lbs/acre, preferably about 4–5 lbs/acre, of the granule of the present invention will provide the same efficacy, i.e. >90% pest control at the site of administration.

Quick Release Granule

The unique and preferred properties of the quick release microbial control granule are:
1. a high density core particle as a carrier, preferably sand, which improves the swath width which can be achieved in ground broadcast applications;
2. improved vegetation canopy penetration due to heavier and smaller particle size;
3. greatly reduced drift or wind displacement of aerially applied granule particles, an inherent problem with light weight granule products;
4. the use of a buoyant agent to deliver the particulate microbial control agent from the pond bottom to the water surface where it is released to be most effectively ingested by target insects;
5. the use of carrier particles in the size ranges which provide for the adequate and effective distribution of microbial control agent in the environment to achieve uniform delivery of control agent in the target insect habitat, such distribution being of great significance for insoluble particulate active ingredients which do not easily achieve uniform distribution in the environment; and 6. the quick (0.1 to 72 hour) release of microbial insect control agent upon flooding with water to deliver a rapid killing quantity of controlling agent to the water surface to be ingested by early developmental stages of target insects which are most susceptible.

Formulation ingredients are combined by uniformly pre-blending the pesticide, preferably the bacterial pesticide, e.g., the Bti primary powder, with the buoyant agent. Next the sand carrier is added to a prilling drum or rotary blender, the drum or blender turned on, and the aqueous adhesive, preferably a fish gelatin, solution sprayed to begin uniformly wetting the sand, then the pre-blended powders are added at the same rate as the adhesive solution. The finished granule is then blended for at least 1 or more minutes to pack the granule contents and drive residual moisture to the granule surface to aid drying. The granule is then dried as needed, bagged and labeled.

Sustained Release Granule

The unique and preferred properties of the sustained or slow release microbial control granule are:

1. features 1 through 6 related above for the quick release granule which also apply to the sustained release granule; and additionally 7. the sustained release of microbial agent over time (10 to 30 or more days), which release is regulated by means of slowly dissolving water soluble adhesive(s) to deliver the microbial insect control agent to the water surface.

Both quick release and sustained release composites are manufactured essentially by a similar process comprising:

1. prilling a core particle having a density greater than water in a mixing apparatus;
2. spraying the prilled particle with an aqueous solution of water soluble adhesive;
3. adding a blend of a floatation agent having a density less than water at the temperature of the use location at about the same rate as the spray delivery of step (2);
4. rolling the resulting prilled composite, and, if desired;
5. adding a drying agent followed by additional rolling of the prilled composite.

As examples of the composites of the present invention, the following tables illustrate the useful and preferred formulations. The examples of the quick release mosquito control composite and the slow release mosquito control composite are meant to be exemplary only and are not limited to mosquito control but can also be used for other pests as in the general description of the controlled release pest control composite. The ingredients are also variable and the specific ingredients illustrated in these tables are for purposes of illustration and not to be limited thereon.

| Controlled Release Pest Control Composite | | |
|---|---|---|
| Ingredient | Useful (wt %) | Preferred (wt %) |
| Core Particle | 75–95 | 80–90 |

| Controlled Release Pest Control Composite -continued | | |
|---|---|---|
| Ingredient | Useful (wt %) | Preferred (wt %) |
| Pesticide | 1.0–15.0 | 2.0–5.0 |
| Floatation Agent | 0.5–5.0 | 3.0–4.0 |
| Water Soluble Adhesive | 0.5–4.0 | 1.0–3.0 |
| Water | 0.0–10.0 | 1.0–8.0 |

| Quick Release Mosquito Control Composite | | |
|---|---|---|
| Ingredient | Useful (wt %) | Preferred (wt %) |
| Sand | 75–95 | 75–88.1 |
| Bti | 2.0–6.0 | 2.0–5.0 |
| Floatation Agent | 2.0–5.0 | 3.0–4.0 |
| Fish Gelatin | 0.5–4.0 | 1.0–3.0 |
| Anionic Surfactant | 0.0–1.0 | 0.005–0.4 |
| Glycerin | 0.0–3.0 | 0.05–2.0 |
| Drying Agent | 0.0–3.0 | 0.10–2.0 |
| Water | 0.0–4.0 | 1.0–2.0 |

| Sustained Release Mosquito Control Composite | | |
|---|---|---|
| Ingredient | Useful (wt %) | Preferred (wt %) |
| Sand | 70–95 | 75–88.1 |
| Bti | 2.0–15.0 | 2.0–15.0 |
| Floatation Agent | 2.0–12.5 | 3.0–12.5 |
| Technical Protein Colloid | 0.5–5.0 | 1.0–3.0 |
| Drying Agent | 0.0–3.0 | 0.10–2.0 |
| Water | 4.0–10.0 | 5.0–8.0 |

The following examples are illustrative of the present invention and particularly describe in more detail the formulations covered by the present invention and their use. These examples are not to be read as limiting the present invention.

EXAMPLE 1

Rapid Releasing Microbial Insect Control Granule For Aquatic Habitats

Insect Control Granule containing *Bacillus thuringiensis israelensis*. Manufacturing recipe to make 1000 pounds:

| INGREDIENT | QUANTITY (lbs.) |
|---|---|
| Premix A: | |
| *Bacillus thuringiensis israelensis* technical powder | 47.0 |
| Dicaperl 920 powder | 37.5 |
| Premix B: | |
| Water | 11.71 |
| Morwet EFW Surfactant | 0.11 |
| Glycerin | 13.7 |
| Gelatin, fish (44.5%) | 20.0 |
| Remaining product ingredients: | |
| Sand, Texas 12/20 Blast Sand | 866.7 |

-continued

| INGREDIENT | QUANTITY (lbs.) |
|---|---|
| Drying Agent | 3.3 |

Premix Manufacturing Procedure:
Premix A:

Uniformly co-blended the *Bacillus thuringiensis israelensis* technical powder with the Dicaperl 920 powder in a sealed powder blender, such as an air, ribbon or rotary blender. The blended material was bagged and held until required.

Premix B:

Blended ingredients thoroughly in a heat jacketed mixer with stirring paddle, maintaining the combined temperature at 130°–140° F. The solution was a viscous brown blend. The temperature did not exceed 150° F.

Product Manufacturing Procedure

1. The granule was prilled by adding the Texas 12/20 sand to a rotary type mixer, such as a Munson or Continental mixer.
2. The mixer was started and the sand was sprayed lightly with a fine spray of Premix solution B using flat fan spray nozzles like Spray Systems 8001 with pressure appropriate to deliver the entire liquid volume in a fine spray within 5 to 7 minutes. The Premix A powders were added with a vibratory unit at a rate which matched the spray delivery rate of Premix B solution.
3. After all powders were added, the prilled granules were rolled for one minute longer. Added Sipernat drying and rolled for 1 additional minute.
4. The batch was discharged and a sample was retained for reference.
5. The granules were sieved to remove excess powders and bagged in unlined triple wall paper bags.

EXAMPLE 2

Slow Releasing Microbial Insect Control Granule For Aquatic Habitats

Insect Control Granule containing *Bacillus thuringiensis israelensis*. Manufacturing recipe to make 1000 pounds:

| INGREDIENT | QUANTITY (lbs.) |
|---|---|
| Premix A: | |
| Bacillus thuringiensis israelensis technical powder | 35.0 |
| Dicaperl 920 powder | 30.0 |
| Premix B: | |
| Water | 65.0 |
| Technical Protein Colloid 90014 | 2.6 |
| Remaining product ingredients: | |
| Sand, Red Flint #30 | 857.4 |
| Drying Agent Sipernat 22 | 10.0 |

Premix Manufacturing Procedure:
Premix A:

Uniformly coblended the *Bacillus thuringiensis israelensis* technical powder with the Dicaperl 920 powder in sealed powder blender, such as an air, ribbon or rotary blender. The blended material was bagged and held until required.

Premix B:

Dissolved ingredients thoroughly in a heat jacketed mixer with stirring paddle, maintaining the combined temperature at 120° F. The solution was a low viscosity light tan. The temperature did not exceed 150° F.

Product Manufacturing Procedure

1. The granule was prilled by adding the Red Flint #30 sand to a rotary type mixer, such as a Munson or Continental mixer.
2. The mixer was started and the sand was lightly sprayed with a fine spray of Premix solution B using flat fan spray nozzles like Spray Systems 8001 with pressure appropriate to deliver the entire liquid volume in a fine fan spray within 5 to 7 minutes. The Premix A powders were added with a vibratory unit at a rate which matched the spray delivery rate of the Premix B solution.
3. When all the powders were added, the prilled granules were rolled for one minute longer. The Sipernat drying agent was added in an amount needed to achieve a free flowing granule after compacted in storage, and rolled for 3 minutes longer.
4. The batch was discharged and a sample retained for reference.
5. The finished granule was bagged in unlined triple wall paper bags.

EXAMPLE 3

Sustained Release Microbial Insect Control Granule For Aquatic Habitats

Insect Control Granule containing *Bacillus thuringiensis israelensis*. Manufacturing recipe to make 1000 pounds:

| INGREDIENT | QUANTITY (lbs.) |
|---|---|
| Premix A: | |
| Bacillus thuringiensis israelensis technical powder | 150.0 |
| Propyltex 140 S Polypropylene powder | 127.0 |
| Premix B: | |
| Water | 108.0 |
| Technical Protein Colloid 90014 | 27.0 |
| Glyoxal 40% | 1.0 |
| Remaining product ingredients: | |
| Sand, Texas 12/20 Blast Sand | 582.0 |
| Drying agent Sipernat 22 | 5.0 |

Premix A:

Uniformly coblended the Bacillus thuringiensis israelensis technical powder with the Propyltex 140 S polypropylene powder in sealed powder blender, such as an air, ribbon or rotary blender. The blended material bagged and held until required.

Premix B:

Dissolved the Technical protein colloid in water thoroughly in a heat jacketed mixer with stirring paddle, maintaining the temperature at 130° F. The solution was a viscous tan blend. The temperature did not exceed 150° F. Added glycerin. When all preparations had been made and spraying was ready to start, added glyoxal solution to the technical protein colloid solution to crosslink the colloid and the mixture was blended for one minute, then immediately spraying was initiated to prill the granule. The spraying was completed within 8 to 10 minutes.

Product Manufacturing Procedure

1. The granule was prilled by adding the Texas 12/20 sand to a rotary type mixer, such as a Munson or Continental mixer.
2. The mixer was started and the sand was sprayed lightly with a fine spray of Premix solution B using flat fan spray nozzles like Spry Systems 8001 with pressure appropriate to deliver the entire liquid volume in a fine fan spray within 7 to 10 minutes. The Premix A powders were added with a vibratory unit at a rate which matched the spray delivery rate of the Premix B solution.
3. When all powders were added, the prilled granules were rolled for two minutes longer. The Sipernat drying agent was added and the granules rolled for 2 minutes longer.
4. The batch was discharged. A sample was retained for reference.
5. The finished granule was bagged in unlined triple wall paper bags.

EXAMPLE 4

Rapid Release Microbial Insect Control Granule For Terrestrial Habitats

Insect Control Granule containing *Bacillus thuringiensis var kurstaki*. Manufacturing recipe to make 1000 pounds:

| INGREDIENT | QUANTITY (lbs.) |
| --- | --- |
| Premix A: | |
| *Bacillus thuringiensis var kurstaki* technical powder | 20.0 |
| Dicaperl 920 powder | 16.0 |
| Premix B: | |
| Water | 8.79 |
| Morwet EFW Surfactant | 0.04 |
| Glycerin | 2.55 |
| Gelatin, fish (44.5%) | 5.61 |
| Remaining product ingredients: | |
| Sand, Texas 12/20 | 944.0 |
| Drying agent Sipernat 22 | 3.0 |

Premix Manufacturing Procedure:
Premix A:

Uniformly coblended the *Bacillus thuringiensis var kurstaki* technical powder with the Dicaperl 920 powder in a sealed powder blender, such as an air, ribbon or rotary blender. The blended material as bagged and held until required.

Premix B:

Blended the ingredients thoroughly in a heat jacketed mixer with stirring paddle, maintaining the combined temperature at 135° F. The solution was a viscous brown blend. The temperature did not exceed 150° F.

Product Manufacturing Procedure

1. The granule was prilled by adding the Texas 20/40 sand to a rotary type mixer, such as a Munson or Continental mixer.
2. The mixer was started and the sand was sprayed lightly with a fine spray of Premix solution B using flat fan spray nozzles like Spray Systems 8001 with pressure appropriate to deliver the entire liquid volume in a fine spray within 5 to 7 minutes. The Premix A powders were added with a vibratory unit at a rate which matched the spray delivery rate of the Premix B solution.
3. When all powders were added, the prilled granules were rolled for one minute longer. The Sipernat drying agent was added and the granules rolled for 1 minute additional.
4. The batch was discharged. A sample was retained for reference.
5. The granules were sieved to remove excess powders and the finished granule bagged in unlined triple wall paper bags.

EXAMPLE 5

Sustained Release Microbial Insect Control Granule For Terrestrial Habitats

Insect Control Granule containing *Bacillus thuringiensis var kurstaki*. Manufacturing recipe to make 1000 pounds:

| INGREDIENT | QUANTITY (lbs.) |
| --- | --- |
| Premix A: | |
| *Bacillus thuringiensis var kurstaki* technical powder | 50.0 |
| Dicaperl 920 powder | 25.0 |
| Premix B: | |
| Water | 25.35 |
| Glycerin | 3.75 |
| Technical Protein Colloid 90014 | 7.50 |
| Glyoxal, 40% | 0.90 |
| Remaining product ingredients: | |
| Sand, Texas 12/40 | 884.5 |
| Drying agent Sipernat 22 | 3.0 |

Premix Manufacturing Procedure
Premix A:

Uniformly coblended the *Bacillus thuringiensis var kurstaki* technical powder with the Dicaperl 920 powder in a sealed powder blender, such as an air, ribbon or rotary blender. The blended material was bagged and held until required.

Premix B:

Dissolved the technical protein colloid thoroughly in water in a heat jacketed mixer with stirring paddle, maintaining the temperature at 135° F. The solution was a viscous brown blend. The temperature did not exceed 150° F. Added glycerin. When the spraying was ready to start, added glyoxal solution to the technical protein colloid solution to crosslink it; blended for one minute, then immediately began spraying to prill the granule. The spraying was completed within 8 to 10 minutes.

Product Manufacturing Procedure

1. The granule was prilled by adding the Texas 20/40 sand to a rotary type mixer, such as a Munson or Continental mixer.
2. The mixer was started and the sand was sprayed lightly with a fine spray of Premix solution B using flat fan spray nozzles like Spray Systems 8001 with pressure appropriate to deliver the entire liquid volume in a fine fan spray within 5 to 7 minutes. The Premix A powders were added with a vibratory unit at a rate which matched the spray delivery rate of the Premix B solution.
3. When all powders were added, the prilled granules were rolled for two minutes longer. The Sipernat drying agent was added and rolling continued for 1 minute longer.
4. The batch was discharged. A sample was retained for reference.
5. The granules were sieved to remove excess powders and the finished granule bagged in unlined triple wall paper bags.

Field Efficacy Trials

Field test results using a quick release formulation prepared by the method of Example 1 in small pools, and applications to natural field mosquito breeding sites have achieved approximately 92–100% control consistently at the operational rate of 5 lbs. of granules/acre.

Field Trial Procedures

The procedure used to evaluate granule formulations in the field is as follows. Once a mosquito breeding site is found containing mosquito larvae, a site map is prepared noting the site number, locations, site description, water depth and water temperature. Immature mosquito larval population levels are then assessed by taking not less than 20 pre treatment dip samples using a standard mosquito dipper and counting the larvae. The number of mosquitoes in each sample is recorded. Pre and post treatment observations on untreated check/reference sites are included to compensate for water level and natural mortality changes which can alter larval numbers in field sites.

The square footage of each site is determined by pacing the average length and width of the water surface. That figure is divided by the number of square feet in an acre to determine the percentage of an acre which the test site represents. To determine the quantity of granule to be applied to each test site, the percentage is multiplied against a standard granule dosage rate of 5 lb./granules per acre used in the trials, and converted to grams to increase the measuring accuracy.

The quantity of granules to be applied to each test site is measured on a gram scale and applied evenly across the water surface using a hand applicator, for example, a hand crank spreader or horn seeder. To achieve uniform application, the total quantity of granules to be applied is divided in half, and half applied over the plot in one direction, and the second half of the granules applied at right angles to the first direction.

Granule control efficacy in each site is determined by monitoring, recording and comparing mosquito larval numbers present in pre and post treatment counts. The number is corrected for changes in untreated/reference larval counts using Mulla's Formula II (Mulla et al., *J. Econ. Entomol.*, 71:774–777, 1971):

% Control=100−(C1/T1×T2/C2) 100 where:

C1=mean number per sample pre-treatment in check

T1=mean number per sample pre-treatment in treated

C2=mean number per sample post-treatment in check

T2=mean number per sample post-treatment in treated

The results of granule field tests are shown in Table 1 and Table 2.

TABLE 1

The biological efficacy of rapid release *Bacillus thuringiensis israelensis* granule formulation in field treatments against *Aedes vexans* mosquito larvae on July 6, 1994.

| Site # | Site Sq. Ft. | Water Depth (inches) | Pre-Treatmt[1] | Post-Treatmt[2] | % Control[3] |
|---|---|---|---|---|---|
| 1 | 180 | 4 | 16.9 | 0.05 | 99.9 |
| 2 | 45 | 3 | 33.5 | 2.1 | 99.9 |
| 3 | 108 | 4 | 12.5 | 0.0 | 100.0 |
| 4 | 132 | 3 | 19.4 | 0.1 | 99.9 |
| 5 | 288 | 6 | 24.6 | 2.2 | 99.9 |
| 6 | 270 | 3 | 6.3 | 0.05 | 99.9 |
| 7 | 750 | 6 | 15.8 | 0.0 | 100.0 |
| 8 | 450 | 3 | 4.9 | 6.8 | control |
| 9 | 840 | 6 | 8.8 | 0.05 | 99.9 |
| 10 | 1,638 | 6 | 200.0 | 1.8 | 99.9 |
| 11 | 405 | 10 | 58.2 | 4.5 | 99.9 |

[1]Average number of mosquito larvae per dip pre treatment.
[2]Average number of mosquito larvae per dip 24 hours post treatment.
[3]Mortality corrected with Mulla's Formula II.

TABLE 2

The biological efficacy of rapid release *Bacillus thuringiensis israelensis* granule formulation in field treatments against *Aedes vexans* mosquito larvae on July 6, 1994.

| Site # | Site Sq. Ft. | Water Depth (inches) | Pre-Treatmt[1] | Post-Treatmt[2] | % Control[3] |
|---|---|---|---|---|---|
| 1 | 990 | 6 | 8.8 | 0.6 | 93.0 |
| 2 | 2,250 | 4 | 64.8 | 0.0 | 100.0 |
| 3 | 540 | 4 | 58.0 | 0.15 | 99.7 |
| 4 | 360 | 3 | 22.0 | 2.95 | 86.2[4] |
| 5 | 540 | 6 | 21.1 | 1.05 | 94.9 |
| 6 | 1,080 | 3 | 67.0 | 1.30 | 98.0 |
| 7 | 1,080 | 12 | 42.2 | 10.05 | 75.6[5] |
| 8 | 1,125 | 12 | 40.8 | 0.4 | 99.0 |
| 9 | 1,890 | 6 | 58.3 | 4.3 | 92.4 |
| 10 | 540 | 5 | 4.0 | 3.9 | control |

[1]Average number of mosquito larvae per dip pre treatment.
[2]Average number of mosquito larvae per dip 24 hours post treatment.
[3]Mortality corrected with Mulla's Formula II.
[4]Site with many small pockets where particles did not reach.
[5]Flowing water diluted treatment.

I claim:

1. A controlled release pest control composite particle adapted for broadcast application, said composite comprising:

(a) about 70 to 95 wt % of a particle having a density greater than water;

(b) about 0.5 to 12.5 wt % of a floatation agent having a density less than water at the temperature of a use location;
(c) an effective pest controlling amount of a pesticide; and
(d) about 0.5 to 5.0 wt % of a water soluble adhesive; wherein the composite particle has a density greater than about 1.0 g/ml and after application, and in contact with water, said adhesive softens causing the composite to disassemble releasing the floatation agent and the pesticide to the surface where the pesticide acts to control a pest population.

2. The composite of claim 1 wherein the pesticide comprises a bacterial pesticide which is present in an amount of about 1.0 to 15.0 wt % of the composite.

3. The composite of claim 2 wherein the bacterial pesticide comprises a *Bacillus thuringiensis*.

4. The composite of claim 3 wherein the *Bacillus thuringiensis* comprises *Bacillus thuringiensis israelensis*.

5. The composite of claim 3 wherein the *Bacillus thuringiensis* comprises *Bacillus thuringiensis var kutstaki*.

6. The composite of claim 1 wherein the core particle comprises sand.

7. The composite of claim 1 wherein the particle is a core particle wherein the water soluble adhesive binds the floatation agent and the pesticide to the core particle.

8. The composite of claim 1 wherein the floatation agent has a specific gravity less than about 0.9 gm/ml.

9. The composite of claim 8 wherein the floatation agent comprises a polypropylene powder.

10. The composite of claim 8 wherein the floatation agent comprises perlite.

11. The composite of claim 1 wherein the adhesive comprises a technical protein colloid.

12. The composite of claim 1 wherein the adhesive comprises an animal gelatin.

13. The composite of claim 1 wherein the adhesive comprises a fish gelatin.

14. The composite of claim 1 wherein the adhesive comprises a polyvinyl alcohol.

15. The composite of claim 1 which further comprises up to about 10.0 wt % water.

16. The composite of claim 1 which further comprises up to about 1.0 wt % of an anionic surfactant.

17. The composite of claim 1 which further comprises up to about 3.0 wt % of a polyol.

18. The composite of claim 1 which further comprises up to about 3.0 wt % of a drying agent.

19. A controlled release pest control composite particle adapted for broadcast application, said composite comprising:
(a) about 75 to 90 wt % of a core particle having a density greater than water;
(b) about 3.0 to 12.5 wt % of a floatation agent having a density less than water at the temperature of a use location;
(c) about 2.8 to 15.0 wt % of a bacterial pesticide;
(d) about 1.0 to 3.0 wt % of a water soluble adhesive which adheres the floatation agent and the pesticide onto the core particle; and
(e) about 1.0 to 8.0 wt % water;
wherein the composite has a density of greater than about 1.10 g/ml, and after application, and in contact with water, said adhesive softens causing the composite to disassemble releasing the floatation agent carrying the pesticide to the surface where the pesticide acts to control pest population.

20. The composite of claim 19 wherein the bacterial pesticide comprises a *Bacillus thuringiensis*.

21. The composite of claim 20 wherein the *Bacillus thuringiensis* comprises *Bacillus thuringiensis israelensis*.

22. The composite of claim 20 wherein the *Bacillus thuringiensis* comprises *Bacillus thuringiensis var kurstaki*.

23. The composite of claim 19 wherein the core particle comprises sand.

24. The composite of claim 19 wherein the floatation agent comprises a polypropylene powder.

25. The composite of claim 19 wherein the floatation agent comprises perlite.

26. The composite of claim 19 wherein the adhesive comprises a technical protein colloid.

27. The composite of claim 19 wherein the adhesive comprises a fish gelatin.

28. The composite of claim 19, further comprising about 0.005 to 0.4 wt % of an anionic surfactant selected from an alkyl sulfate or alkylarylsulfonate and mixture thereof.

29. The composite of claim 19, further comprising about 0.5 to 2.0 wt % of glycerin.

30. The composite of claim 17, further comprising about 0.10 to 2.0 wt % of a drying agent.

31. A quick release mosquito control composite particle adapted for broadcast application comprising:
(a) about 75 to 95 wt % sand;
(b) about 2.0 to 5.0 wt % of a floatation agent having a density less than water at the temperature of a use location;
(c) about 2.0 to 6.0 wt % of a *Bacillus thuringiensis*; and
(d) about 0.5 to 4.0 wt % of a fish gelatin; wherein the composite particle has a density greater than 1.0 g/ml.

32. A sustained release mosquito control composite particle adapted for broadcast application comprising:
(a) about 70 to 95 wt % sand;
(b) about 2.0 to 12.5 wt % of a floatation agent having a density less than water at the temperature of a use location;
(c) about 2.0 to 15.0 wt % of a *Bacillus thuringiensis*;
(d) about 0.5 to 5.0 wt % of a technical protein colloid; and
(e) about 4.0 to 10.0 wt % water; wherein the composite particle has a density greater than 1.0 g/ml.

33. A method for controlling pests which comprises applying by broadcast means a controlled release pest composite particle as claimed in claim 1 onto aqueous sites or sites that have episodic rainfall, wherein:
(a) on contact with water said composite particle sinks and softens causing the composite to release a mixture of a floatation agent and a pesticide; and
(b) which mixture rises to the surface of the water where the pesticide is released in a timed controlled manner.

34. The method of claim 33 wherein the composite comprises:
(a) about 80 to 90 wt % of a core particle having a density greater than water;
(b) about 3.0 to 4.0 wt % of a floatation agent having a density less than water at the temperature of the use location in admixture with about 2.0 to 5.0 wt % of a bacterial pesticide;
(c) about 1.0 to 3.0 wt % of a water soluble adhesive to adhere the floatation agent and pesticide onto the core particle; and
(d) about 1.0 to 8.0 wt % water.

35. A method of controlling mosquito populations comprising:

(1) applying by broadcast means to a body of water a controlled release composite particle, said composite comprising:
 (a) about 80 to 90 wt % of a core particle having a density greater than water;
 (b) about 3.0 to 4.0 wt % of a floatation agent having a density less than water at the temperature of the use location in admixture with about 2.0 to 5.0 wt % of a *Bacillus thuringiensis*;
 (c) about 1.0 to 3.0 wt % of a technical protein colloid or fish gelatin to adhere the mixture of the floatation agent and strain on the core particle; and
 (d) about 1.0 to 8.0 wt % water;
(2) on contact with water, said composite sinks and softens causing the release of a mixture of the floatation agent and bacteria; and
(3) said mixture rises to the surface of the body of water releasing in a timed control manner the bacteria.

36. A method of manufacturing a controlled release pest control composite particle comprising:
 (1) prilling a core particle having a density greater than water in a mixing apparatus;
 (2) spraying the prilled core particle with an aqueous solution of a water soluble adhesive;
 (3) adding a blend of a floatation agent having a density less than water at the temperature of the use location and a pesticide at about the same rate as the spray delivery of step (2);
 (4) rolling the resulting prilled composite, and, if desired;
 (5) adding a drying agent in step (3) or following step (4) followed by additional rolling of the prilled composite.

37. The process of claim 36 wherein the core particle is sand.

38. The process of claim 36 wherein the pesticide is a bacterial pesticide.

39. The process of claim 38 wherein the bacterial pesticide is a *Bacillus thuringiensis*.

40. The process of claim 39 wherein the *Bacillus thuringiensis* is *Bacillus thuringiensis israelensis* or *Bacillus thuringiensis var kurstaki*.

41. The process of claim 36 wherein the floatation agent is a polypropylene powder or perlite.

42. The process of claim 36 wherein the aqueous solution of the water soluble adhesive comprises an aqueous solution of a technical protein colloid or a fish gelatin.

43. The process of claim 42 wherein the aqueous adhesive solution further comprises an anionic surfactant.

44. The process of claim 43 wherein the anionic surfactant is an alkyl sulfate or alkylarylsulfonate and mixtures thereof.

45. The process of claim 42 wherein the aqueous adhesive solution further comprises a polyol.

46. The process of claim 45 wherein the polyol is glycerin.

* * * * *

UNITED STATES PATENT AND TRADEMARK OFFICE
CERTIFICATE OF CORRECTION

PATENT NO. : 5,484,600

DATED : January 16, 1996

INVENTOR(S) : Sjogren

It is certified that error appears in the above-identified patent and that said Letters Patent is hereby corrected as shown below:

In Column 14, line 43, "July 6," should read --July 20,--.

In Column 14, line 53, #7, "75. 6$^{5/}$" should read --75.6$^{5/}$--.

Signed and Sealed this

Twenty-third Day of July, 1996

Attest:

BRUCE LEHMAN

Attesting Officer     Commissioner of Patents and Trademarks